(12) United States Patent
Koizumi

(10) Patent No.: US 9,239,279 B1
(45) Date of Patent: Jan. 19, 2016

(54) SEQUENTIAL DIFFERENTIAL MOBILITY ANALYZER AND METHOD OF USING SAME

(75) Inventor: Hideya Koizumi, Jonesboro, AR (US)

(73) Assignee: Arkansas State University—Jonesboro, State University, AR (US)

(*) Notice: Subject to any disclaimer, the term of this patent is extended or adjusted under 35 U.S.C. 154(b) by 727 days.

(21) Appl. No.: 13/488,174

(22) Filed: Jun. 4, 2012

Related U.S. Application Data

(60) Provisional application No. 61/493,212, filed on Jun. 3, 2011.

(51) Int. Cl.
| | | |
|---|---|---|
| G01N 15/02 | (2006.01) | |
| H01J 49/02 | (2006.01) | |
| G01N 27/62 | (2006.01) | |

(52) U.S. Cl.
CPC .......... *G01N 15/0266* (2013.01); *G01N 27/624* (2013.01); *H01J 49/025* (2013.01)

(58) Field of Classification Search
CPC .................... G01N 2001/2223; G01N 27/624; G01N 15/0266; H01J 49/025; B01D 59/44
See application file for complete search history.

(56) References Cited

U.S. PATENT DOCUMENTS

| | | | | |
|---|---|---|---|---|
| 5,214,386 A | * | 5/1993 | Singer et al. | 324/452 |
| 6,230,572 B1 | * | 5/2001 | Pui et al. | 73/863.21 |
| 6,498,313 B1 | * | 12/2002 | Stencel et al. | 209/131 |
| 6,607,597 B2 | | 8/2003 | Sun et al. | |
| 6,787,763 B2 | | 9/2004 | De La Mora et al. | |
| 6,809,314 B2 | * | 10/2004 | Yamada et al. | 250/288 |
| 7,161,143 B2 | | 1/2007 | De La Mora et al. | |
| 7,213,476 B2 | | 5/2007 | Cheng | |
| 7,361,212 B2 | * | 4/2008 | Clark et al. | 96/69 |
| 7,471,076 B2 | * | 12/2008 | Ahn | 324/71.4 |
| 7,521,673 B2 | | 4/2009 | Arcas et al. | |
| 7,549,318 B2 | * | 6/2009 | Burtscher et al. | 73/28.02 |
| 7,723,677 B2 | | 5/2010 | Ramiro Arcas et al. | |
| 7,836,751 B2 | * | 11/2010 | Marra | 73/28.02 |
| 7,880,109 B2 | * | 2/2011 | Okuda et al. | 209/129 |
| 8,698,076 B2 | * | 4/2014 | Orii et al. | 250/294 |
| 8,739,602 B2 | * | 6/2014 | Vize et al. | 73/28.02 |

OTHER PUBLICATIONS

Saito, Kenichiro, Eiko Koizumi, and Hideya Koizumi. "Application of Parallel Hybrid Algorithm in Massively Parallel GPGPU—The Improved Effective and Efficient Method for Calculating Coulombic Interactions in Simulations of Many Ions with SIMION." Journal of The American Society for Mass Spectrometry 23.9 (2012): 1609-1615.*

(Continued)

*Primary Examiner* — Lisa Caputo
*Assistant Examiner* — Punam Roy
(74) *Attorney, Agent, or Firm* — Schrantz Law Firm, PLLC; Stephen D. Schrantz

(57) ABSTRACT

The invention is essentially a sequential ("DMA") apparatus using a novel arrangement of at least three electrodes and at least two block electrodes to produce a DMA apparatus having at least two sequential DMA regions between pairs of adjacent electrode walls within the same housing. This apparatus is used to improve the transfer of particles into the subsequent DMA region without a vacuum or pump, and to improve the separation of target particles from non-target particles and concentration and collection of the target particles.

17 Claims, 16 Drawing Sheets

(56) References Cited

OTHER PUBLICATIONS

Figure 1:
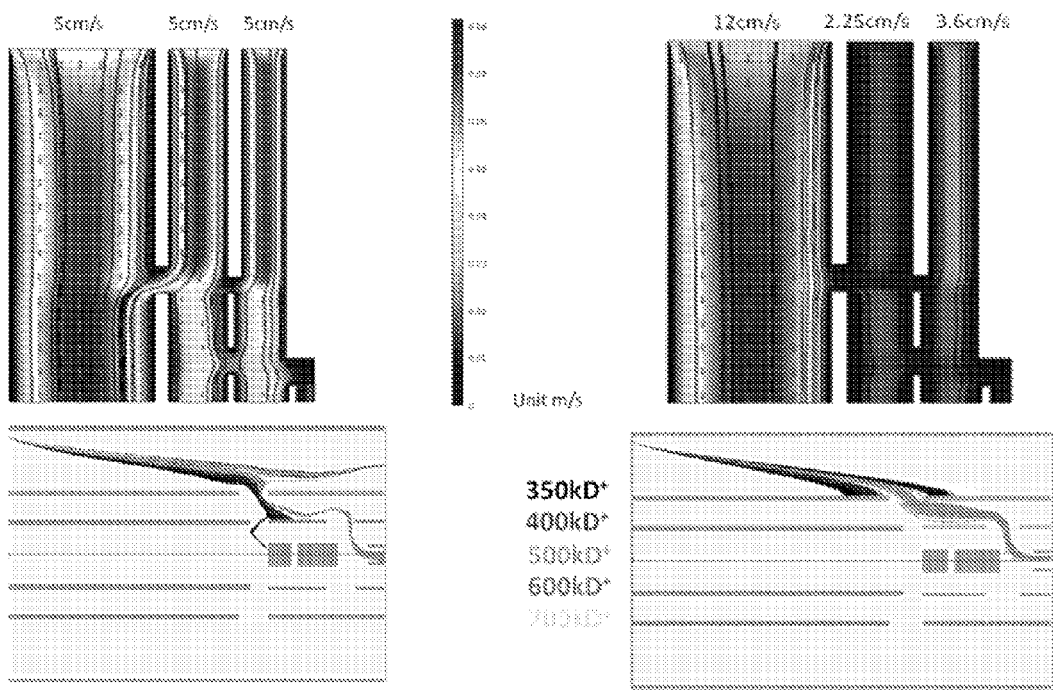
Figure 2:
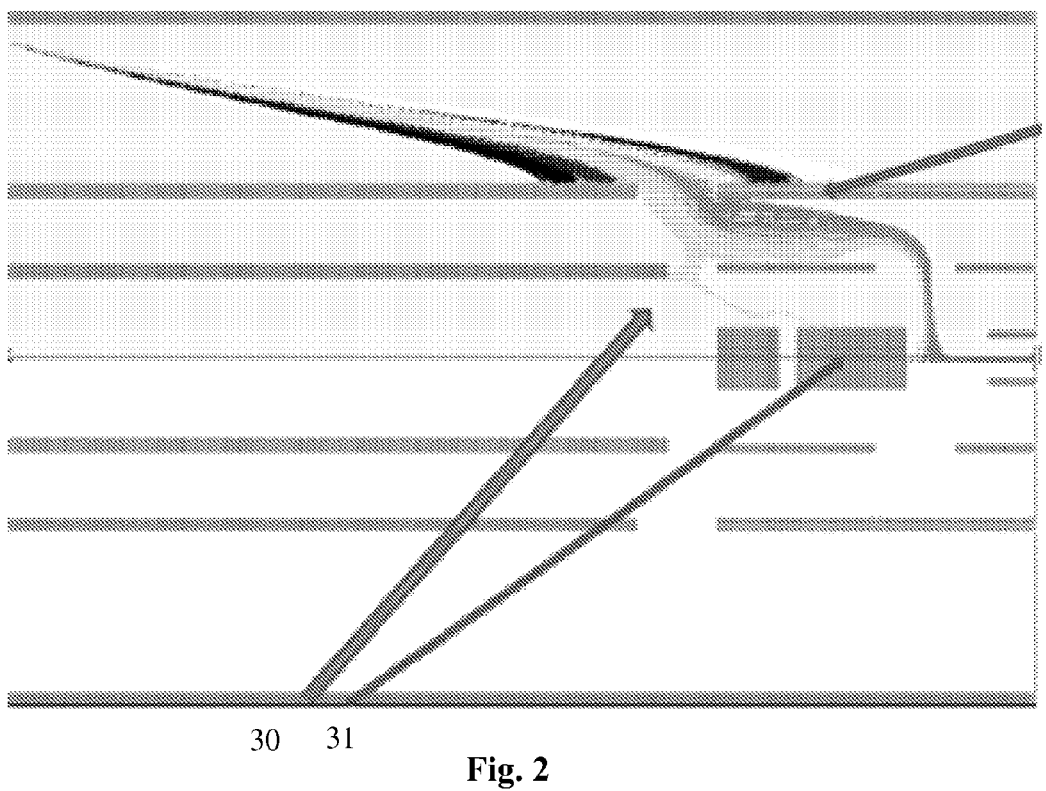
Figure 3:
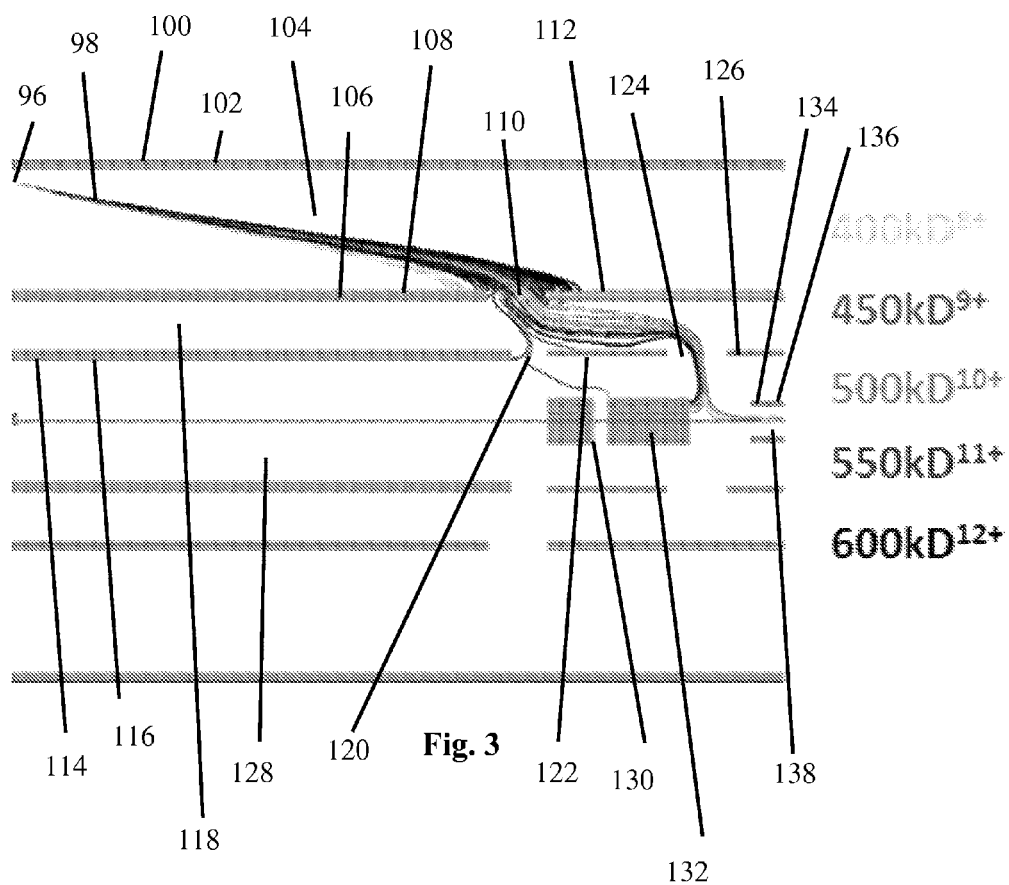

Orii, Takaaki and Kudoh, Satoshi, "Development of a Double-Layer Differential Mobility Analyzer (DLDMA)", International Aerosol Conference Aug. 29-Sep. 3, 2010 (Organized by International Aerosol Research Assembly and Finnish Association for Aerosol Research (FAAR).*

Rosell-Llompart, J. I. G. D. J., et al. "Sizing nanoparticles and ions with a short differential mobility analyzer." Journal of Aerosol Science 27.5 (1996): 695-719.*

* cited by examiner 30  31

SEQUENTIAL DIFFERENTIAL MOBILITY ANALYZER AND METHOD OF USING SAME

CROSS-REFERENCE TO RELATED APPLICATIONS

This application claims the benefit of U.S. Provisional Application No. 61/493,212, filed Jun. 3, 2011, the content of which is incorporated herein by reference.

FEDERALLY SPONSORED RESEARCH AND DEVELOPMENT

Not applicable.

MICROFICHE APPENDIX

Not applicable.

BACKGROUND OF THE INVENTION (1) Field of the Invention.

The present invention generally relates to a sequential differential mobility analyzer for separating and concentrating the size of selected target ions or charged target particles (collectively "Target Particles"). More particularly, the invention disclosed herein primarily uses a combination of differential aerodynamic mobility and differential lateral electrical mobility, within sequential regions having both airflow(s) and electrical field(s), to separate Target Particles (having a targeted size and electronic charge) from other particles.

A differential mobility analyzer ("DMA") is an instrument typically used to separate small charged aerosol particles based on their electrical mobility, for detection and classification. Many DMAs include two charged concentric cylindrical electrodes, creating an electric field between adjacent electrode walls. This essentially annular pathway (or annular region) between adjacent electrodes may be considered the analysis region. Also included is an aerosol inlet for introducing sample particles (including Target Particles) into the instrument. A sheath gas inlet permits sheath gas (or sheath gas, collectively "sheath gas") to flow into the instrument between the electrodes, which draws the polydispersed particles through the annular region.

In most cases, the resolution of the DMA is limited by diffusion, turbulence, initial spatial distribution of particles, and the ratio of aerosol flow to sheath flow which relates to the transfer function of the particles.

One disadvantage with using only two electrodes is that traditionally there is only one drift region of electrical field inducing differential lateral drift of different particles due to each particle's electrical charge and aerodynamic diameter.

Another disadvantage with using traditional tandem or sequential DMAs is that they do not include a plurality of analysis regions within the same housing, and fewer target particles will be separated en route to the instrument exit. The typical sequential DMA setup will not materially increase the resolution above that of its individual DMA components.

Yet another disadvantage of a regular DMA is that sheath flow through the gap in electrodes is directed inwardly toward the central exit. This is required to improve the particle transport efficiencies only because classified aerosol flow which contains only target particles are suctioned by the external pump. This flow direction reduces the resolving power of the instrument because it does not prevent the diffusive crossing of unwanted particles (including neutral particles).

Another disadvantage of existing DMAs is that target particles are diluted because the classified aerosol flow rate is high or fast, to achieve sufficient transport efficiencies. Consequently, possible coupling devices such as a mass spectrometer cannot utilize all the particles in the classified aerosol flow. In this regard, the detection efficiencies are severely limited.

(2) Description of Related Art Including Information Disclosed 37 CFR 1.97 and 1.98.

The electrical mobility of a charged particle is inversely related to the particle's size; smaller particles exhibit greater mobility within an electrical field than do larger particles (of like charge). Conversely, larger particles travel more in a "downwind" direction during its longer residence time in the drift region due to their smaller electrical mobilities. By calibrating and coordinating the parameters of both the airflow and the gradient(s) of the electrical field(s) transversing the airflow route(s), smaller-than-targeted particles can be electronically attracted while larger-than-targeted particles continue being swept downstream with the airflow, so that only the Target Particles exit the instrument. Ideally only the Target Particles, having the desired electrical mobility and particle size, are extracted from the analyzer.

The following patents are arguably material to the patentability of the invention disclosed herein:

| patent/App. # | 1st Inventor | Date of Issue/Publication |
| --- | --- | --- |
| 6,607,597 | Sun et al. | Aug. 19, 2003 |
| 6,787,763 | De La Mora et al. | Sep. 7, 2004 |
| 7,161,143 | De La Mora et al. | Jan. 9, 2007 |
| 7,213,476 | Cheng et al. | May 8, 2007 |
| 7,521,673 | Arcas et al. | Apr. 21, 2009 |
| 7,723,677 | Ramiro Arcas et al. | May 25, 2010 |

U.S. Pat. No. 7,723,677 issued to Ramiro Arcas et al. essentially discloses a DMA having an electric field component opposite to the drag flow to cause the main electric field to be oblique to the velocity field of the drag flow, rather than perpendicular to the velocity field of the drag flow. It discloses a control volume with a rectangular base in which two opposing walls made up of electrodes define an electric field. The two remaining opposite sides of the region form an inlet and outlet of the ordinary cross flow, which is perpendicular to the electrodes. It also discloses the usage of resistive electrodes or conductive electrodes separated by insulators to achieve an electric field against the sheath flow inside the controlled volume. With the external circuit being open or closed, the controlled volume can be switched from classic DMA to DMA utilizing oblique fields against the sheath flow. The device contains shared controlled volume as well as a single inlet with multiple exit slits. One of the exit slits located upstream is used when the device is used as DMA with oblique field.

U.S. Pat. No. 7,213,476 issued to Cheng et al. essentially discloses a multi-stage DMA for aerosol measurements including a first electrode having at least one inlet for receiving an aerosol including charged particles for analysis. A second electrode is spaced apart from the first electrode, and has at least one sampling outlet disposed at a plurality of different distances along its length. A volume between the first and second electrode between the inlet and one of the outlets forms a classifying region, with the first and second electrodes for charging to suitable potentials to create an electric field within the classifying region. The inlet in the first electrode receives a sheath gas flow at an upstream end of the classifying region, wherein each sampling outlet functions as an independent DMA stage and simultaneously classifies different size ranges of charged particles based on electric mobility. The aerosol is preferably injected from a central electrode and the sampling flow is preferably withdrawn through an outer electrode.

None of the cited patents expressly disclose a sequential DMA analyzer having a housing enclosing electrodes forming a plurality of sequential DMA analysis regions without overlap of controlled volume for analyzing a Target Particle, with the sample aerosol intended to initially travel downstream with the sheath flow without pump assistance, and including a plurality of guide electrodes for guiding Target Particles to the exit outlet.

BRIEF SUMMARY OF THE INVENTION

Although the present invention has several embodiments, the version generally described is essentially a method and apparatus for separating charged Target Particles or ions in a sequential differential mobility analyzer. The apparatus essentially comprises (includes) a housing enclosing a novel arrangement of electrodes forming a 1st DMA analysis region and a $2^{nd}$ DMA analysis region, and utilizing guide electrodes for guiding Target Particles between the DMA regions and toward an exit while diverting non-target particles. Sheath gas is applied through a sheath gas inlet to facilitate particle movement in an essentially linear downstream direction, preferably via laminar airflow. The gas or air sample, containing both Target Particles and non-target particles, is introduced into the apparatus through an upstream sample inlet. The two DMA analysis regions are formed between pairs of adjacent electrode walls within the same housing. This apparatus is used to improve the transfer of particles into the subsequent DMA analysis region with minimal volume flow rate of carrier gas containing highly concentrated polydispersed aerosol, to improve the separation of Target Particles from non-target particles, and to otherwise improve the DMA resolution and analytic capabilities.

An electric field is established in each analysis region between the electrodes, by DC voltage power supply. Electrical mobility is the ability of charged particles to travel through a medium in response to an electrical field that is attracting or repelling them.

Figure 4:
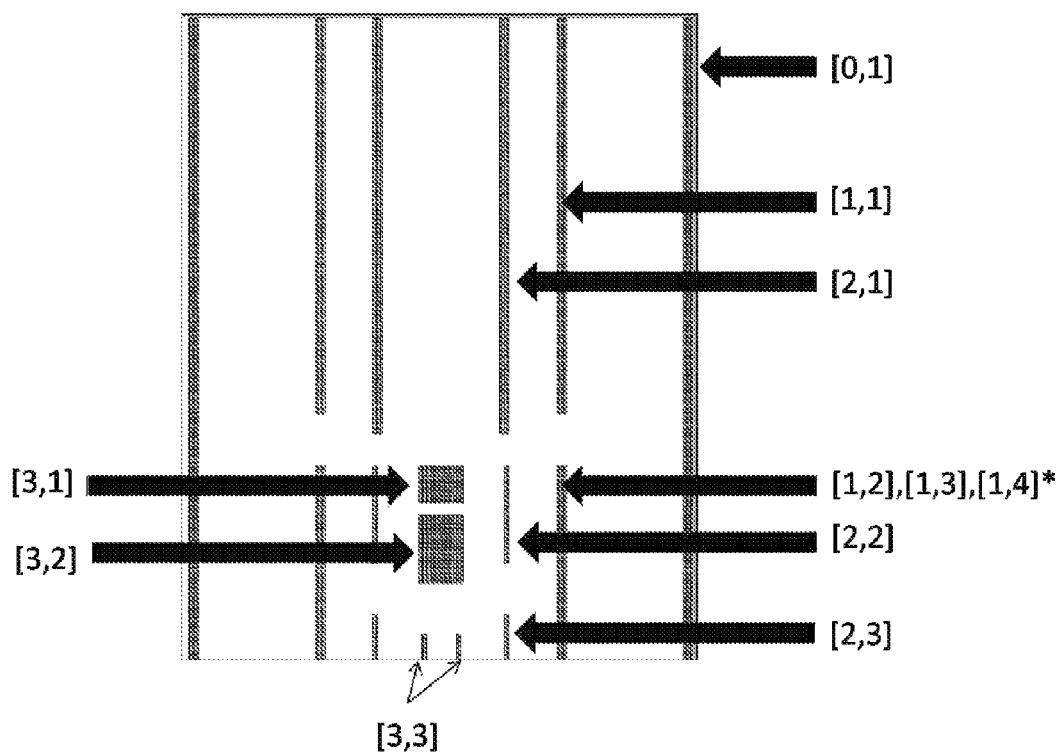
Figure 5:
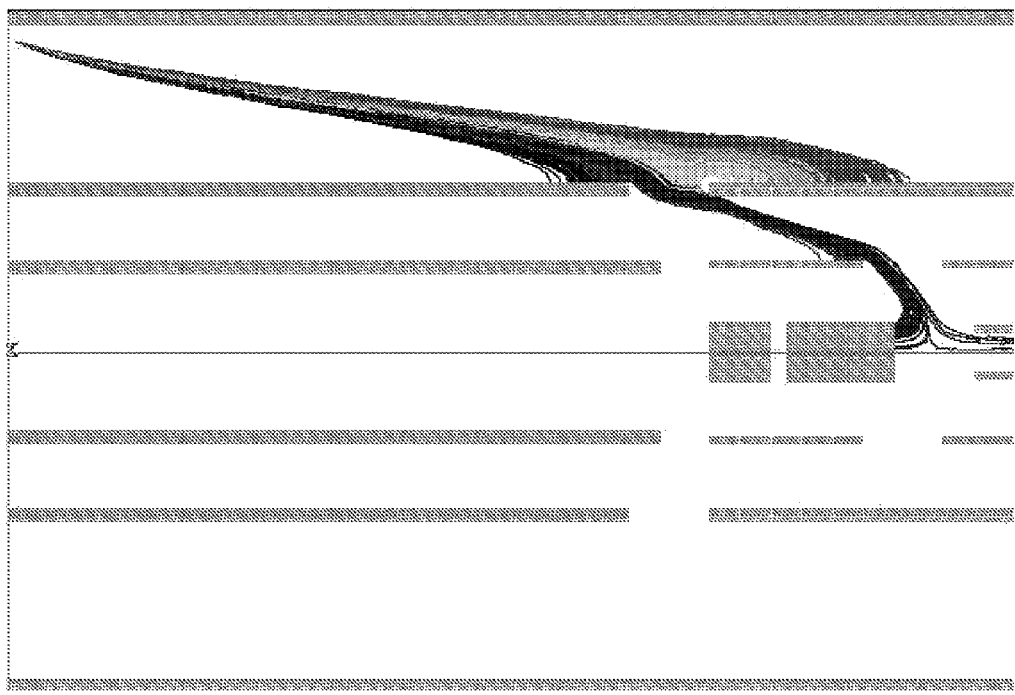
Figure 6:
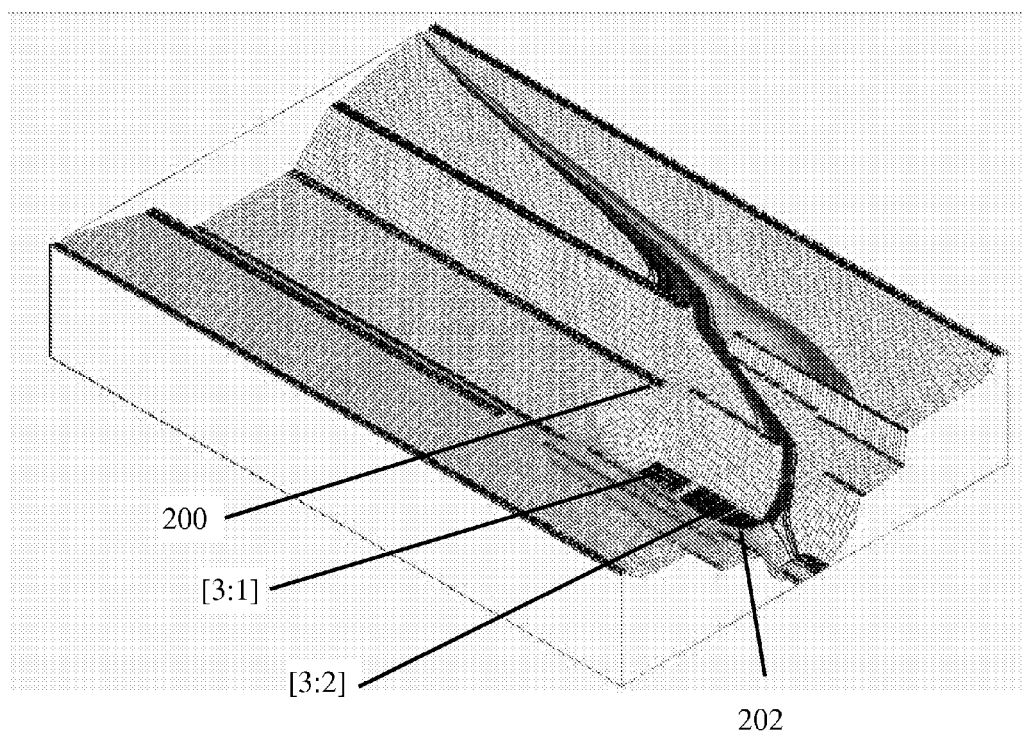

Using the labels of FIG. 4, as the particles travel along the essentially annular pathway between adjacent pairs of electrodes (grounded-housing 0 and medial-electrode 1), non-target particles either migrate downstream or are lost at the electrode wall (1,1) and (1,2), leaving particles having an electrical mobility closer in range to the Target Particles' electrical mobility. A gap exists between the upstream segment of the medial electrode (1,1) and the downstream segment of the medial electrode (1,2) to allow these particles to continue travelling toward the exit for capture or analysis. At this junction, another elimination step occurs and the smaller particles migrate toward the upper segment of the central electrode (2,1), some perhaps migrating upstream toward the downstream tip of the upper segment of the central electrode (2,1). The remaining particles travel into the 2nd DMA analysis region, where non-target particles are primarily attracted to the middle section of the central electrode (2,2) and the lower section of the central electrode (2,3). The smaller particles will be further attracted to (and eliminated by) electrodes (3,2) and exit electrode (3,3). At the final elimination stage, only the Target Particles are available for extraction at the exit outlet.

In general, the invention disclosed herein includes an improved differential mobility analyzer apparatus for analyzing a sample of airborne particles, said apparatus comprising a housing encompassing a plurality of concentric electrodes having walls defining a plurality of airflow pathways and flow rates and a plurality of electrical fields therein for facilitating differential movement of airborne particles from an upstream end of the housing toward a downstream exit end comprising a central exit electrode-tip. Each respective electrode wall also includes a gap allowing lateral drifting of some of the airborne particles from an outer of the airflow pathways into an inner of said airflow pathways enroute to the exit electrode-tip. The upstream end of the housing further comprises a sample gas inlet providing the sample of polydispersed aerosol particles to an outermost first of said airflow pathways, and a sheath gas inlet providing sheath gas to all of the airflow pathways.

More particularly, the housing includes a cylinder having a grounded housing sidewall; the plurality of electrodes includes a concentric cylindrical arrangement within the grounded housing sidewall. One of the electrodes includes a medial electrode nearest the housing having an upstream segment and a downstream segment separated by a midstream gap. The downstream segment terminates in the end wall. The medial electrode and the grounded housing sidewall define the first airflow pathway therebetween.

One of the electrodes may be a central electrode (2) within the medial electrode, and having an upper section and a middle section separated by a middle gaplet, such as the first outer opening between the first outer wall and the second outer wall. The upper section of the central electrode includes a gaplet-tip, an extension of the first inner wall, that extends further downstream than the upstream segment of the medial electrode. One primary purpose of the gaplet-tip is to attract and assist elimination of non-target particles that migrate through the gap, even pulling some of such particles upstream against the sheath flow under the appropriate combination of voltage, sheath flow and particle size. In addition, it reduces the Target Particle loss at downstream medial electrodes by pulling the Target Particles inward and away from the downstream segment of medial electrode. The upper section of the central electrode also includes an electrical voltage substantially more negative than that of the upstream segment of the medial electrode. The aggregate downstream length of the gaplet-tip and the gaplet is approximately that of the midstream gap between the upper and lower segments of the medial electrode. In one embodiment, the gaplet-tip extends approximately four-tenths of the downstream length of the gap.

The downstream segment of the medial electrode and the middle section of the central electrode and the first block electrode (3,1) commence at essentially the same relative position immediately downstream of the gap. The potential applied to middle section of the central electrode may be set at more negative than that of the opposite portion(s) of the downstream segment of the medial electrode but less than that of the second block electrode (3,2). The central electrode also has a lower section separated from the middle section by a cleft, with the lower section of the central electrode terminating downstream in the end wall. The central electrode and the medial electrode define a second airflow pathway therebetween. The central electrode defines a third airflow pathway to the exit electrode-tip; a first block electrode (3,1) and a second block electrode (3,2) are situated within the third airflow pathway. The apparatus preferably includes a means of selecting the voltage applied separately to each of the segments and sections and portions.

One primary object of the present invention is to provide at least two non-overlapping sequential DMA analysis regions within the same housing to improve the transfer of particles from one DMA region into a second DMA region without a vacuum or with the minimal assist of a vacuum, thus making this apparatus ideal for a mass spectrometer inlet.

Another primary object of the present invention is to provide at least two sequential DMA regions within the same housing to improve separation of Target Particles from non-target particles.

Another object of the invention is to provide a DMA apparatus that does not require the use of a pump for classified sample aerosol flow.

Another object of the invention is to provide a guide electrode to enhance the highly efficient transfer of particles into the second inner DMA.

Another object of the present invention is to separate particles using electrical fields which induce particle movement independent of that created by the sheath flow.

Other objects will be apparent from a reading of the written description disclosed herein, together with the claims. It would be advantageous to use an analyzer having at least three electrodes, two block electrodes, and at least two DMA regions within the same housing for detection, classification and concentration of Target Particles to maximize both transfer and isolation efficiencies.

BRIEF DESCRIPTION OF THE SEVERAL VIEWS OF THE DRAWINGS

FIG. 1 depicts the airflow of two operational modes, with the left-side showing an outward cross flow mode and the right-side showing a no cross flow mode.

FIG. 2 shows the separation of groups of ions having different size, by the version of the invention depicted in FIG. 4.

FIG. 3 shows the separation of the groups of ions having same m/z ratio, by the version of the invention depicted in FIG. 4.

FIG. 4 depicts a longitudinal cross-section view of another representative sample of the apparatus, with some electrode segments or sections (such as the downstream segment of electrode 2) divided into portions (such as [1,2] and [1,3] and [1,4]).

FIG. 5 depicts a cross-section view, with particles paths, by the version of the invention depicted in FIG. 7.

FIG. 6 depicts a 3-dimensional rendering using a cross-flow mode DMA apparatus having 19 electrodes with applied voltage, the version of the invention depicted in FIG. 7. The different colors or shades represent singly charged particles of different mass, shown as 300 kd 325 kD, 400 kD, 450 kD, and 500 kD, respectively.

FIG. 7 depicts a longitudinal cross-section view of another representative sample of the apparatus, with some electrode segments or sections (such as the downstream segment of electrode 2) divided into portions (such as [1,2],[1,3],[1,4], [1,5], [1,6], [1,7] and [1,8]).

FIG. 8 depicts a longitudinal cross-section view of one representative sample of the apparatus, illustrating the proportions of downstream distances 4:6 of the gaplet-tip and the gap, showing the longitudinal lengths of the first outer aperture compared to the first inner aperture and the extension of the second block electrode downstream of the most longitudinal upstream position of the second inner aperture. FIG. 8 also shows the longitudinal distances 4:6 between the most downstream position of the first inner aperture and first outer aperture compared to the second inner aperture.

FIG. 9 depicts a 3-dimensional rendering of electrical field gradients of the apparatus of FIG. 8 having one arrangement of voltages applied to respective electrodes.

FIG. 10 depicts another embodiment of the apparatus as a cross-section view, with particles paths and with arrows indicating the approximate locations of sheath gas inlets and outlets.

FIG. 11 depicts another close-up view of FIG. 10.

FIG. 12 is a schematic primarily illustrating the electrode portions attracting particles smaller than Target Particles.

FIG. 13 is a schematic of removal of larger particles.

FIG. 14 depicts a perspective longitudinal cross-section view of a 3-D rendering of the invention, showing the sheath gas for the inner cylinder, the aerosol entrance (360° slit), a laminator to make laminar straight air flow, and sheath gas for the outer cylinder.

FIG. 15 depicts a perspective longitudinal cross-section view of a 3-D rendering of FIG. 14.

FIG. 16 depicts a close-up view of a part of FIG. 4, illustrating that electrode portion 1,2 extends undivided from the midstream gap downstream to the downstream wall; a space or insulation material separates electrode portion 1,2 from electrode portions 1,3 and 1,4 on the opposite side, and a space or insulation material separates electrode portion 1.3 from 1.4. Accordingly, each electrode portion is capable of having a different voltage/charge than another portion.

These drawings illustrate certain details of certain embodiments. However, the invention disclosed herein is not limited to only the embodiments so illustrated. The invention disclosed herein may have equally effective or legally equivalent embodiments.

DETAILED DESCRIPTION OF THE INVENTION

For the sake of simplicity and to give the claims of this patent application the broadest interpretation and construction possible, the following definitions will apply:

The term "airflow" essentially means the flow of gas which may include aerosol mixture; unless the context dictates otherwise, any reference to "air" is not limited to the gaseous mixture comprising atmospheric air.

The phrase "differential mobility analyzer" essentially means an apparatus isolating like target particles from an initially polydispersed sample using a combination of electrical fields and a flow of carrier gas, and possibly sheath gas.

The term "electrode" essentially means an electrically conductive structure, or alignment of electrically conductive sections or segments (and/or portions thereof) that together comprise the structure, regardless of whether any section or segment (and/or portion thereof) receives the same electrical voltage as any other. Even though a section or segment (and/or portion thereof) may receive an electrical voltage different and/or independent from that of another section or segment (and/or portion thereof), all within the same structural alignment may be referred to collectively as an electrode; alternatively, any individual section or segment (and/or portion thereof) may be referred to separately as an electrode.

The invention disclosed herein is not limited by construction materials to the extent that such materials satisfy the structural and/or functional requirements. For example, any electrode material may be used so long as it satisfies the function for which it is being used, such as conducting electricity and facilitating formation of an electrical field gradient.

Similarly, the invention is not limited to any particular embodiment described or depicted herein. For example, for illustration purposes, this disclosure primarily focuses upon positively charged Target Particles that are attracted to negatively charged regions of an electrical field, hence the ranges of negative electrical voltages disclosed for such attraction of positively charged Target Particles. However, it should be understood that the invention disclosed herein also includes electrical fields necessary for negatively charged Target Particles.

Mass spectrometry currently allows analyses of particle size up to 100 kD safely, owing to the technological advances in ionization methods and inlets. However, mass analysis of large biomolecules and aerosols from a mixture samples is generally difficult, especially when the mixture is low in concentration. Efficiencies of transport of such large particles into a mass spectrometer in ambient condition are severely hindered because of the limiting flow. Flow field generated by a limiting orifice at ambient condition is weak, and large molecules must be nearly static to be picked up efficiently by the mass spectrometer. This invention is a mass pre-filter device which produces nearly no flow at the transfer point. It is also useful to classify mixtures by mass, shape and density. The design and its computational results of the invention are also disclosed herein.

This invention is a high pressure target particle isolator using at least three concentric electrodes (a housing enveloping a medial inner electrode which envelops a central inner electrode), each inner electrode having at least one spacing allowing lateral migration of Target Particles from a first outer DMA region to a second inner DMA region within the same housing. The apparatus does not require using a pump for the flow of sample aerosol or sheath gas. Thus, a sample containing polydispersed particles is not necessarily pushed or pulled through the apparatus by a pump system. A small amount of a pumping, however, may be used for the improvement of the particle transfer efficiency. However, this invention improves the transfer of particles into the subsequent DMA region without a pump, and improves separation and collection of Target Particles. In typical operation, if any cross flow of sheath gas is desired, such cross flow may be directed from an inner airflow pathway into an outer airflow pathway.

In one embodiment, three concentric tubes or electrodes (a central and medial tube, and a housing tube) essentially form two sequential DMA regions between pairs of adjacent tube walls, and with an innermost airway exit pathway through the central tube. Airflow from the first upstream DMA region into the second downstream DMA region is enabled by a gap in the wall of the medial tube.

Two operational modes are shown in FIG. 1, that may vary from a traditional pump assisted inward flow mode. On the left of FIG. 1 is the outward cross flow mode of the present invention, where some sheath gas flows (or migrates along a pressure gradient) laterally outward through the gap in the medial electrode and into the adjoining annular pathway of an analysis region. On the right side of FIG. 1 is the no cross flow mode, where essentially no sheath gas crosses the gap for entry into the adjoining annular pathway. Streamlines of sheath gas flow, and gas velocity fields are shown here for two different inlet conditions: a) the inlet condition for the outward cross flow mode creates streamlines crossing a gap almost perpendicular to the aerosol trajectories and b) the inlet condition for the no cross flow mode generates the flow to prevent streamlines from crossing the gap. In either case, the flow rate at the aerosol exit is kept extremely low while achieving high aerosol transfer efficiencies. Complete separation of particles having $d_e$=11.3 nm and 11.7 nm is achieved. The inlet flow profile is assumed generated by a "flow laminator". The pathways of target particles in each mode are similar except the voltages on electrodes and flow rate in each of the regions are different. Example voltage and flow rates are given in the Table 1.

TABLE 1

| Voltage set for no cross flow mode target 500KD with given flow condition | | Voltage target 500kD with given flow condition | |
|---|---|---|---|
| Electrode | Applied Voltage in Volts (V) | Electrode | Applied Voltage in Volts (V) |
| (0,1) | 0 | (0,1) | 0 |
| (1,1) | −297 | (1,1) | −105 |
| (1,2) | −300 | (1,2) | −105 |
| (1,3) | −370 | (1,3) | −820 |
| (1,4) | −450 | (1,4) | −1500 |
| (2,1) | −450 | (2,1) | −1450 |
| (2,2) | −380 | (2,2) | −875 |
| (2,3) | −500 | (2,3) | −1800 |
| (3,1) | −500 | (3,1) | −2500 |
| (3,2) | −1700 | (3,2) | −4500 |
| (3,3) | −4000 | (3,3) | −6750 |

FIGS. 8 and 9 show the applied voltages at electrodes (cylindrical walls) and gap alignments. The pair of inner block electrodes ([3,1] and [3,2]), having voltages of −200 V and −570 V in this embodiment, may have solid or mesh construction; and both can be placed at the locations as in the diagram by any means appropriate. The width of the exit pathway is narrower than the block electrodes.

The first, outermost DMA region includes an outermost electrode and medial electrode, and serves as a first filtering stage. The outermost DMA region is located between the inner wall of the housing (electrode (0,1) and the outer wall of the medial electrode (1,1) and (1,2); (FIG. 4). Each electrode is essentially a concentric tube having an electrically conductive wall for attracting particles of opposite charge or repelling particles of the same charge. The electrical field in the 1st DMA region can be chosen in such a way that target particles of a particular electric mobility and aerodynamic diameter will be transported near the gap between the medial electrode (1,1) and medial electrode (1,2). Immediately after the aerosol sample of polydispersed particles is injected into the outermost airflow pathway, ideally the larger-than-target particles are essentially swept downstream by the sheath flow; failing to travel through the lateral gap between the medial electrode (1,1) and (1,2), these larger particles ideally are either attracted (and bound) to the medial electrode wall (1,2), or they exit the apparatus in the sheath flow (and likely get trapped in any filter before any recirculation of sheath gas). Ideally the smaller-than-target particles are attracted (and bound) to the medial electrode (1,1). Non-target particles of size similar to the Target Particles (along with Target Particles) will enter the gap and migrate into the 2nd DMA region between the medial electrode (1,3), (1,4) and central electrode (2,2) and (2,3); see (FIG. 4).

The medial electrode portions (1,3), (1,4) and central electrode sections (2,2) and (2,3), shown in FIG. 4, continue an air flow pathway near the exit end of the apparatus. Preferably there is a space or insulation material between the sidewalls of medial electrode portions (1,3) and (1,4), and the inner sidewall of electrode portion (1,2); preferably there may also be a space or insulative material between the downstream end of electrode portion (1,3) and the upstream end of electrode portion (1-4). Such material may be insulative or dielectric. Electrode portions (1,3) and (1,4) primarily function to remove untargeted particles which happened to pass through the first DMA region and the gap; electrode sections (2,2) and (2,3) may assist is such endeavors. The first block electrode (3,1) primarily functions to attract and eliminate non-target particles in the central airflow pathway. Downstream in the central airflow pathway is a second block electrode (3,2). A cleft between the middle and lower sections of the central electrode primarily functions to allow the flow of Target Particles from the 2nd DMA region into the central airflow pathway enroute to the exit electrode [3,3]. Under the appropriate combination of voltage, airflow and particle size, the second block electrode may facilitate a sharp turn of migrating particles through the cleft. Particles slightly smaller than Target Particles will be attracted to electrode (3,2) and eliminated, whereas Target Particles will move toward the final exit electrode. The primary function of the second block electrode (3,2) is to attract (and trap) smaller-than-target particles that have escaped the upstream electrodes of both DMA regions.

In some embodiments, each segment of the medial electrode (or tube) may include two concentric almost-adjoining sub-segments separated by a dielectric (or insulator). Alternatively, each segment or sub-segment may be further divided into rings almost-adjoined end-to-end, separated by a dielectric (or insulator); one example is electrode portions (1,3) and (1,4). The insulating space between them may be about 200 micron. Upstream ring (1,3) eliminates larger non-target particles so that these particles adhere to this ring (1,3).

The block electrodes (3,1) and (3,2) enhance the highly efficient transfer of particles into the 2nd DMA and exit tube by curving the Target Particles inward by the electric field. The gaplet-tip 200 also assists by being positioned slightly upstream of the middle of the gap, to facilitate efficient transfer of the Target Particles into the second (subsequent) DMA region(s) with more favorable initial position distributions of the Target Particles and non-targeted particles, as well as removal of smaller untargeted particles which happen to pass through the gap (FIGS. 6-7). The second block electrode (3,2) is positioned upstream of the exit tube, which is essentially in the innermost annular flow region. The second block electrode includes a cleft-tip 202, an extension of the second block electrode, extending further downstream than the middle section of the central electrode. The exit electrode-tip defines a lumen having a diameter less than the diameter of the block electrode (3,2).

The position of the block electrodes is such that only smaller particles get attracted toward them, and either get trapped on the electrode or (if a Target Particle) drift closer to the center of the central airflow pathway to align with the exit electrode. Smaller particles may travel toward a block electrode against the sheath flow in the transition or annular region, resulting in a sharp low-mass cut-off in the size distribution. Larger particles are swept downstream by the continuous flow of sheath gas or eliminated by the high-mass filter electrode (1,3). Electrode (1,4) may prevent the loss of Target Particles at electrode (2,2) as they enter the second DMA region, by attracting them in the opposite direction. In an embodiment optimized for collecting Target Particles (rather than identifying or analyzing them), electrode (1,3) may serve as repeller plate for guiding electrode (3,2) to enhance the efficient Target Particle transfer.

The outer diameter of the exit electrode [3,3] is smaller than the diameter of the second block electrode [3,2] to promote better elimination of the particles larger than the Target Particles to prevent them from exiting through the exit electrode. The outer wall of the narrow exit serves as a final filtering stage. Because the second block electrodes guide most of the particles into the exit tube, thereby reducing the particle loss at the wall surface, the transfer function of the apparatus is improved over current technology.

In one embodiment, the upstream segment and downstream segment of the medial electrode may have an electrical voltage of −100 volts. The upper section of the central electrode may have an electrical voltage of −500 volts; the middle section of the central electrode may have an electrical voltage of −125 volts; and the lower section of the central electrode may have an electrical voltage of −125 volts. The first block electrode may have an electrical voltage of −200 volts, and the second block electrode may have an electrical voltage of −570 volts. The exit electrode-tip may have an electrical voltage of −500 volts.

In another embodiment, the controlled volume of the differential mobility classifier can be constructed as shown in FIG. 4 with applied voltage listed in Table 1. However, the voltage on each electrode, section, segment or portion thereof may be different than just recited, and each may vary independently of the others in accordance with the needs of the user and the circumstances of the project at hand.

FIG. 11 is a longitudinal cross-section view of one embodiment of the apparatus. Particles are guided inward by guide electrode (Arrow 18) and block electrodes (Arrow 13). Arrow 10 of FIG. 11 represents an electrode that is a blocker to prevent the particles from going downstream. Arrow 11 points to the direction of the sheath flow. Arrow 17 points to the outside electrode wall. Arrow 18 points to a guide electrode. Arrow 19 points to the first DMA region, while Arrow 20 points to the second DMA region. Arrows 12 and 13 point to the smaller particles that are eliminated by the local electric field produced by the block electrode, which is just enough to move at least some of those particles upstream. The heavier particles will get drifted by sheath flow. Arrow 14 shows where larger particles are eliminated by the upmost tip or outer surface of the exit tube electrode because they are too heavy to get into the exit tube (Arrow 15), which has a smaller diameter (high-mass filter). The apparatus will guide the particles well into the exit tube so not much of particle loss occurs there.

A sample of charged polydispersed aerosol particles is injected into the outermost airflow pathway at inlet 16, which is then mixed with sheath gas. During the 1st DMA filtering stage, a portion of smaller non-target particles drift laterally to the wall surface of electrodes (1,1) and eliminated within the 1st DMA region while larger particles are eliminated by the surface of the electrode (1,2). The remaining aerosol particles then migrate downstream with the sheath flow, at the same velocity as the sheath flow. The radial velocity of a particle due to the movement in response to the electrical field is determined by the particle's electrical mobility, Z, defined by $v_e = Z\Delta V$ where $v_e$ is the electrophoretic migration velocity and $\Delta V$ is the magnitude of the electrical field.

Due to the mobility created by voltage difference between the applied voltages of the outermost electrode (0,1) and middle (medial) electrodes (1,1) and (1,2), positively charged particles in the target size range drift laterally toward the medial electrode with the electrophoretic migration velocity. Once the flow rate of the sheath flow and voltage difference between two electrodes are set in the apparatus, only the particles with certain electrical mobility are transferred efficiently through the gap between the upper and lower segments of the medial electrode, and into the 2nd DMA region. Particles having different electrical mobilities, and lighter than those in the target size, will collide with the wall of electrode (1,1) and will not make it through the gap, and they are thereby separated from the main aerosol stream.

Any non-target particles that incidentally remain in the main airflow stream after passing through the gap are immediately attracted to the wall of the central electrode (2,1) and high mass filter electrode (1,3), and consequently eliminated from the main airflow stream. The wall of the central electrode (2,1) may also include a gaplet-tip extending downstream past the adjacent gap of the medial electrode wall, for attracting more non-targeted particles that have migrated through the gap and into the 2nd DMA region.

Smaller particles migrate quickly to electrode (2,1)_due to the local strong electric field overcoming the aerodynamic force acting on the particles by the sheath flow, while larger particles enter and traverse the 2nd DMA region due to their larger aerodynamic diameter, or are eliminated by the high-mass filter electrode (1,3). Some non-target particles remain on the central electrode wall. The larger non-targeted particles enter the 2nd DMA region at its outer annular region while Target Particles enter the 2nd DMA region at its inner annular region.

Figure 12:
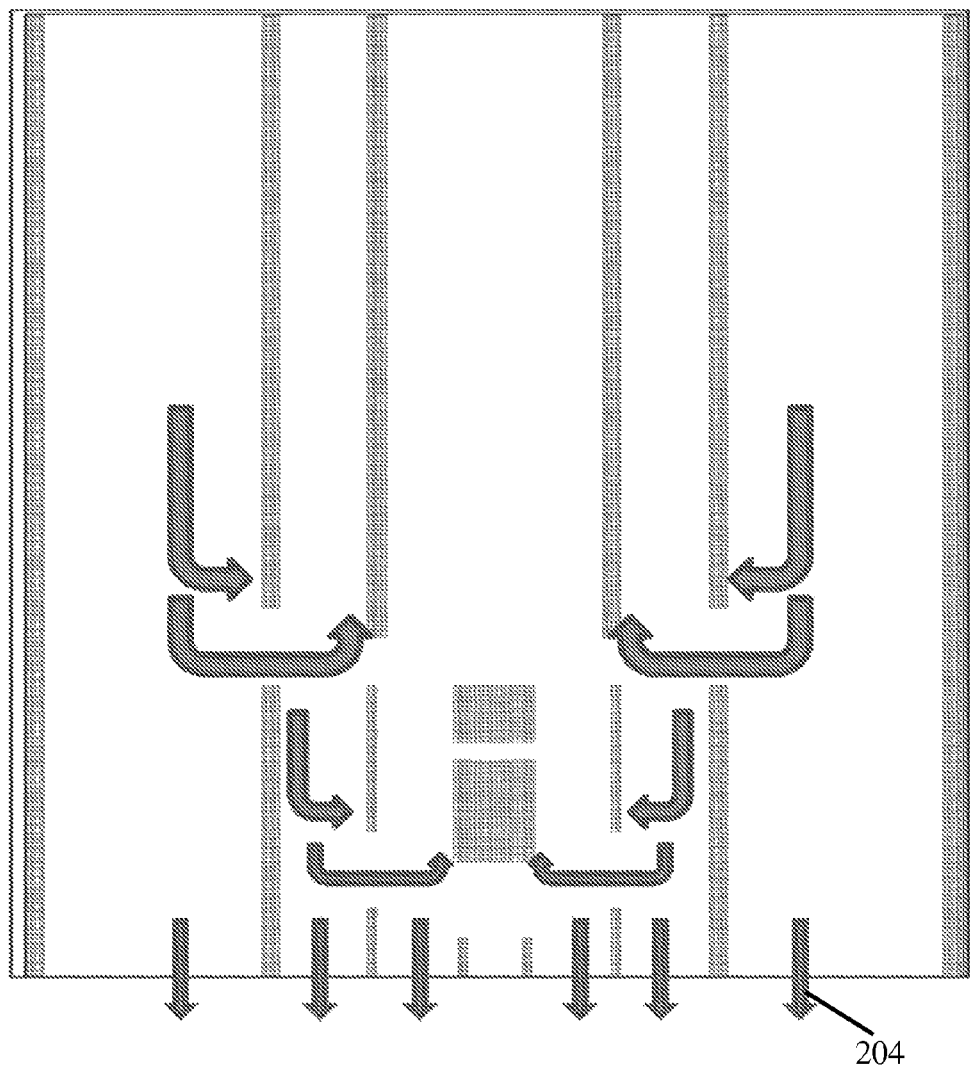

FIG. 12 is a schematic of elimination of particles smaller than the Target Particles. Smaller particles either collide with the wall of the medial electrode just above the gap, or get attracted to the electrode inside the gap and collide with it, and leave the main aerosol stream and follow the sheath flow out into the recirculation path 204.

Figure 13:
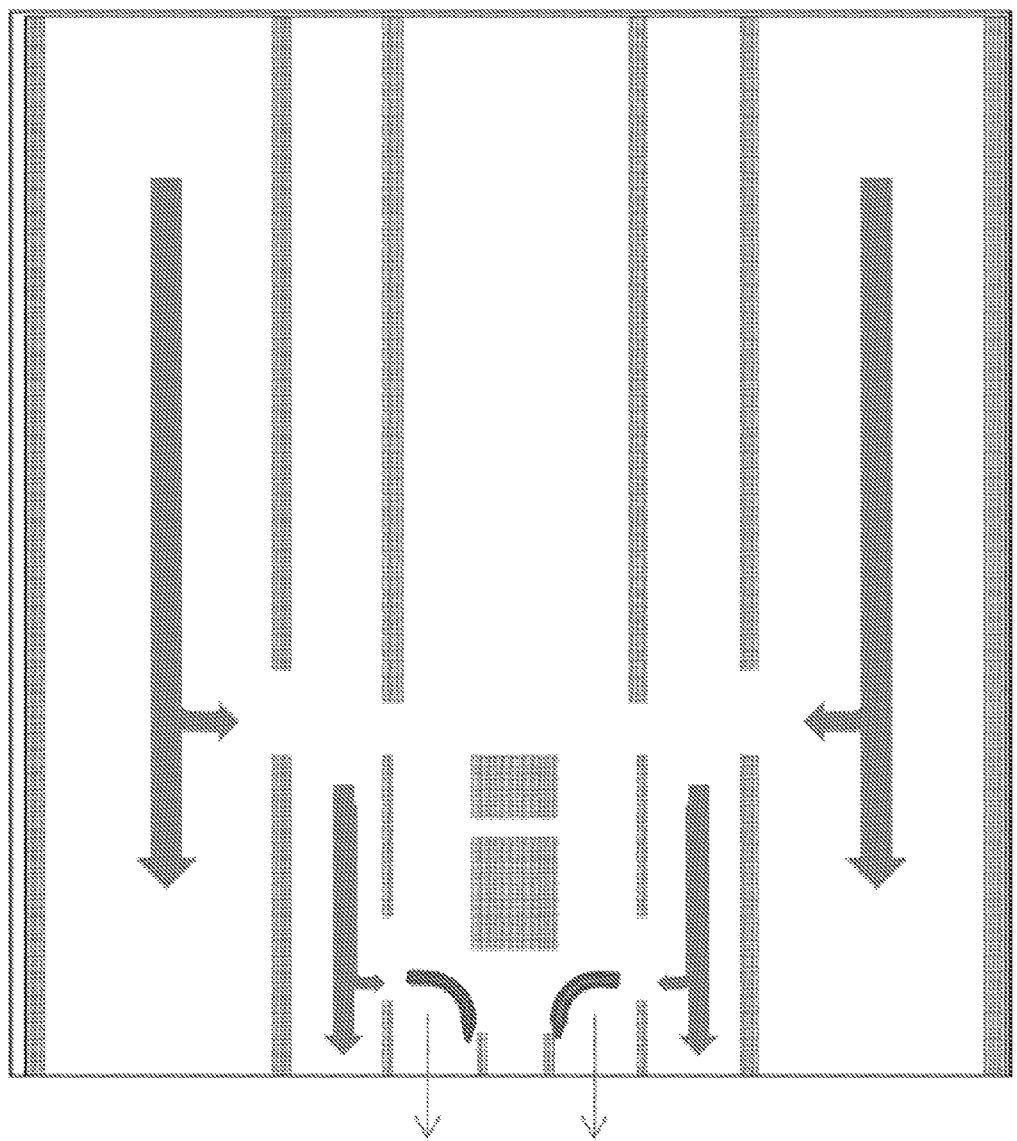
Figure 14:
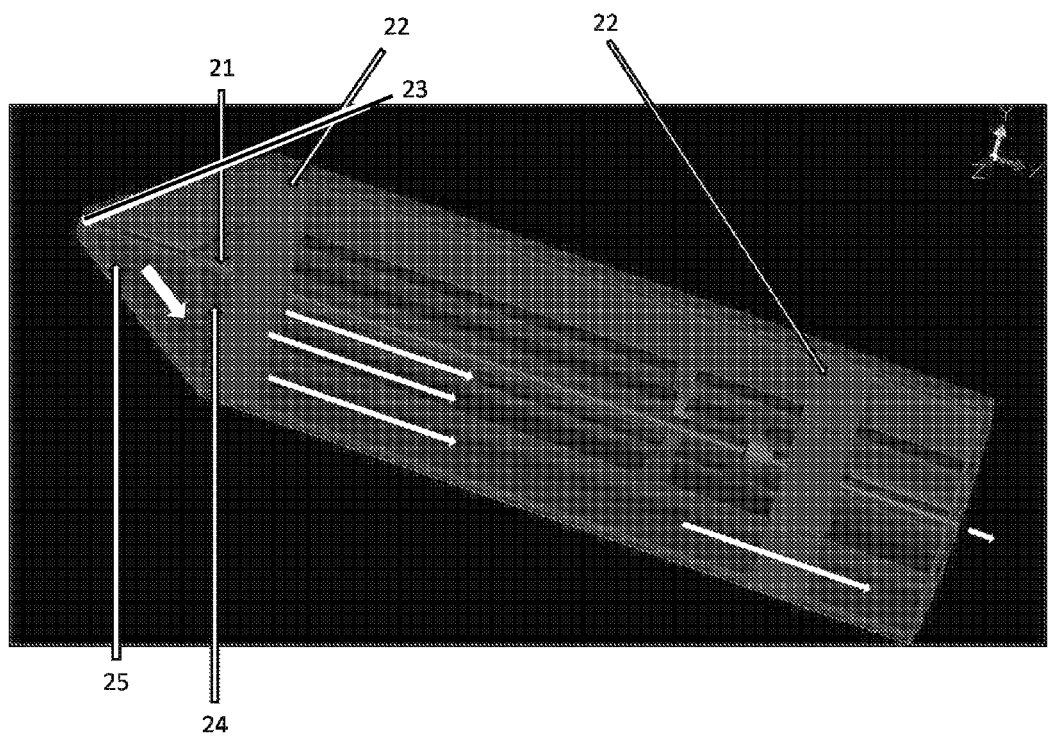
Figure 15:
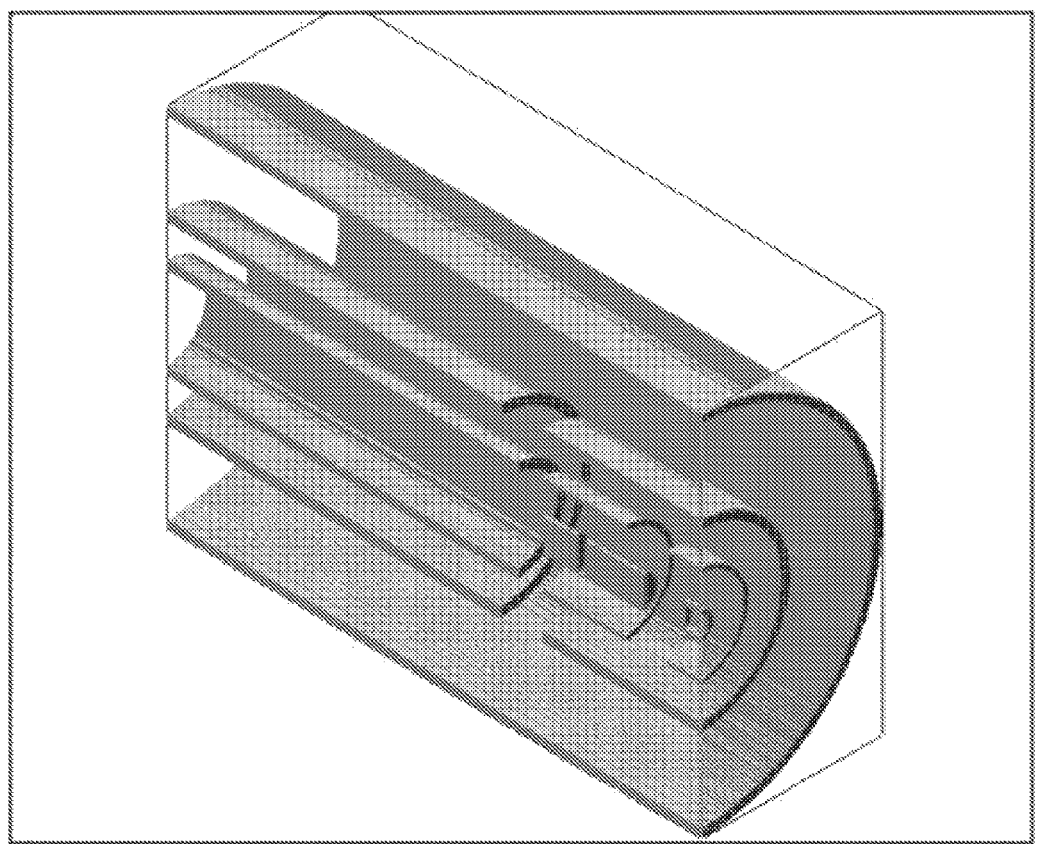
Figure 16:
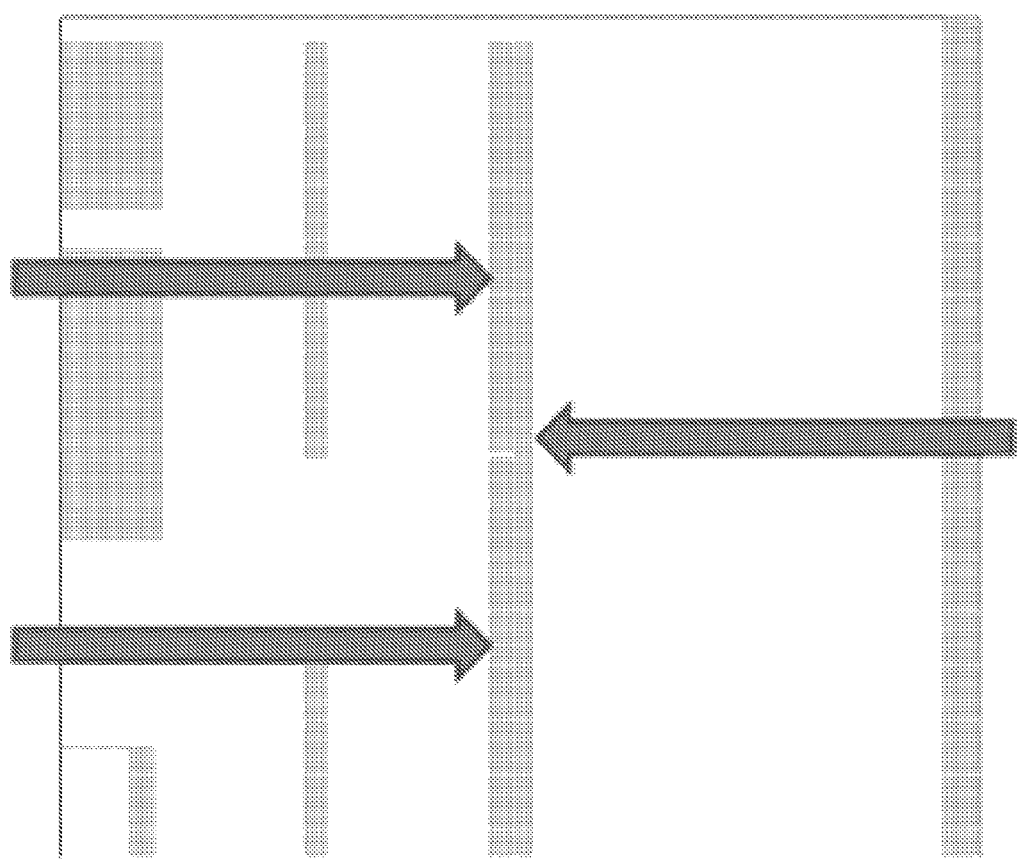

At the last filtering stage, the larger non-target particles (that migrate through the cleft between the middle and lower sections of the central electrode) enter the narrow, converging airway and are swept away or lost at the outer surface as well as upmost tip of the exit tube while non-target particle slightly smaller than the target particle will get attracted by the second block electrode (3,2), allowing only Target Particles to exit the apparatus through exit tube. FIG. 13 is a schematic of removal of larger particles. The widths of the arrows are relative to the concentrations. The larger particles collide with the outside surface (near the top) of the bottom electrodes (1,2) and/or (2,3) and/or (3,3) immediately below the gap or cleft or swept away by the sheath flow. FIG. 14 is the 3-dimensional rendering of the invention. Arrows 21, 24, and 25 point to the sheath air inlets for the central cylinder, the medial cylinder and the outer cylinder, respectively. Arrow 22 points to the laminator (flow straightener), while Arrow 23 points to the Aerosol entrance (360° slit).

The migration of the aerosol particles through the gap (or the gaplet, or the cleft) is essentially induced by the electrical field, unlike those driven by the inward air flow created by pumping the sheath gas out through the exit seen in previous DMA apparati. The air flow created by such a suction apparatus is no longer plug flow near the gap, which is often used in the modeling process in the computer and ultimately result in errors in the calculated resolution and precision.

In the 2nd DMA region, the refined aerosol undergoes the same electrical/airflow filtration process that occurred in the 1st DMA region. Ideally, Target Particles flow through the 2nd DMA region without colliding (or bonding) with the surface of the central electrode (2,2). The non-target particles that are smaller than the Target Particles either collide with the surface of the central electrode wall or are attracted to the second guide electrode, which is placed upstream of the innermost annular flow region of the exit tube.

The electric field produced by the second guide electrode (3,2) attracts all smaller particles inward (and perhaps against the sheath flow), while the remaining particles travel downstream with the sheath gas. Because the sheath gas flow limits the interaction of the strong electric field generated by the second guide electrode, the amount of inward drift is a function of the size of the smaller particles. Larger particles do not drift laterally as much as the smaller particles, and essentially are swept downstream with the airflow. The remaining particles that are larger than the Target Particles can be eliminated by the outer wall of the exit tube. The outer wall of this narrow exit serves as another filter stage for the larger particles. Ideally, only the Target Particles exit the apparatus.

The first and second block electrodes (3,1) and (3,2) could be constructed with metallic, conductive mesh structures or materials to create a uniform electric field near them, as well as minimum disturbance to the uniform plug sheath flow inside the hollow central electrode. As mentioned previously, a large portion of Target Particles within a polydispersed sample travel sufficiently away from the inner wall of the exit electrode, so that the wall loss of the particles by van de Waal interaction is minimized, thus achieving the highly efficient transfer of the Target Particles.

Although it is not necessary to use any external pump to remove particles, a small amount of outward pumping could be used to assist in a better particle transfer. However, the local flow field should only be affected near the exit electrode, without interfering with the gap at the first selection stage. Since the usage of a pump is minimal and the aerosol flow can be greatly reduced because of the highly efficient transfer, it could also help in achieving the creation of highly monodispersed aerosol.

Because the first and second guide electrodes will guide most of the particles into the exit tube, thereby reducing the particle loss at the wall surface, the transfer function of the particles in the first DMA region is given by:

$$\Omega(Z, Z*) = \max\left\{0, \min\left\{1, \frac{\frac{Z}{Z^*} + \beta - 1}{\beta - \beta\delta}, \frac{1 + \beta - \frac{Z}{Z^*}}{\beta - \beta\delta}\right\}\right\}$$

$$\beta = \frac{Q_a + Q_c}{Q_{Sh} + Q_e}, \delta = \frac{Q_a - Q_c}{Q_a + Q_c}$$

where $Q_a$ is the volumetric flow rate of the aerosol flow, $Q_{sh}$ is the volumetric flow rate of the sheath flow, $Q_c$ is the volumetric flow rate of the classified sample flow, and $Q_e$ is the volumetric flow rate of the exhaust flow. The value of $\beta$ shows the resolving power of the DMA; while $\delta$ reveals imbalance between the two flows of aerosol. The probability that a particle of mobility Z will be transmitted from the aerosol flow to the classified aerosol flow when the instrument is set to classify particles of mobility Z* is called the transfer function of the classifier and donates $\Omega(Z, Z^*)$.

The transfer function $\Omega$ is ideal when $\beta$ is small but allowable range is somewhat limited when collection efficiency is far from ideal. Efficient particle transfer and separation reduces the use of gas.

The 2nd DMA region will repeat the same procedure for movement and elimination of non-target particles, however, the second block electrode (3,2) is slightly thicker than the exit tube to promote better elimination of larger particles. The inner radius of the exit tube electrode is narrower to promote better separation from larger particles.

Any of the variables or combinations of the variables, voltage applied to electrodes, sheath gas in the 1st DMA region, sheath gas in the 2nd DMA region, can be scanned for the analysis of the particle distribution in polydispersed particle with appropriate particle detector.

Typical differential mobility analyzers require a significant amount of classified aerosol flow ($Q_c$) to achieve satisfactory transfer efficiency. However, low flow rate $Q_c$ is desired for mass spectrometers, and finding a good balance of efficiency and resolving power is difficult in some cases. Any inward cross flow could wrongly guide larger non-target molecules through the gap if they happen to diffuse toward it during the flight.

Figure 7:
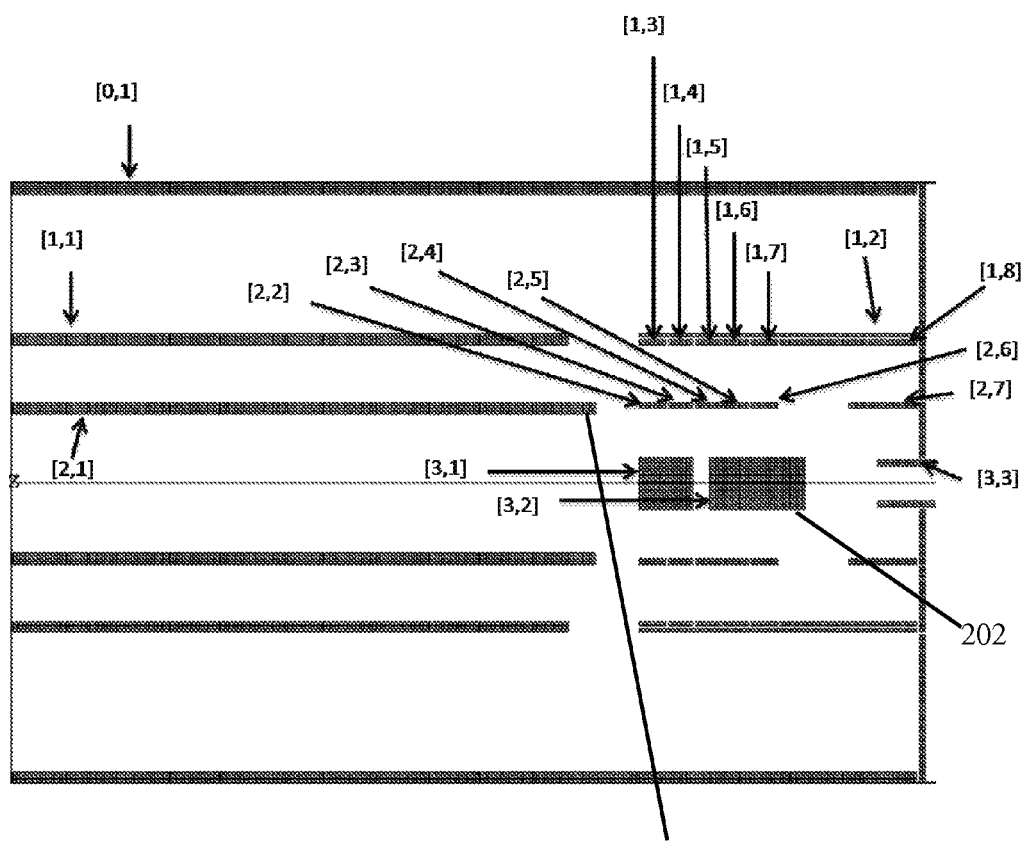
Figure 8:
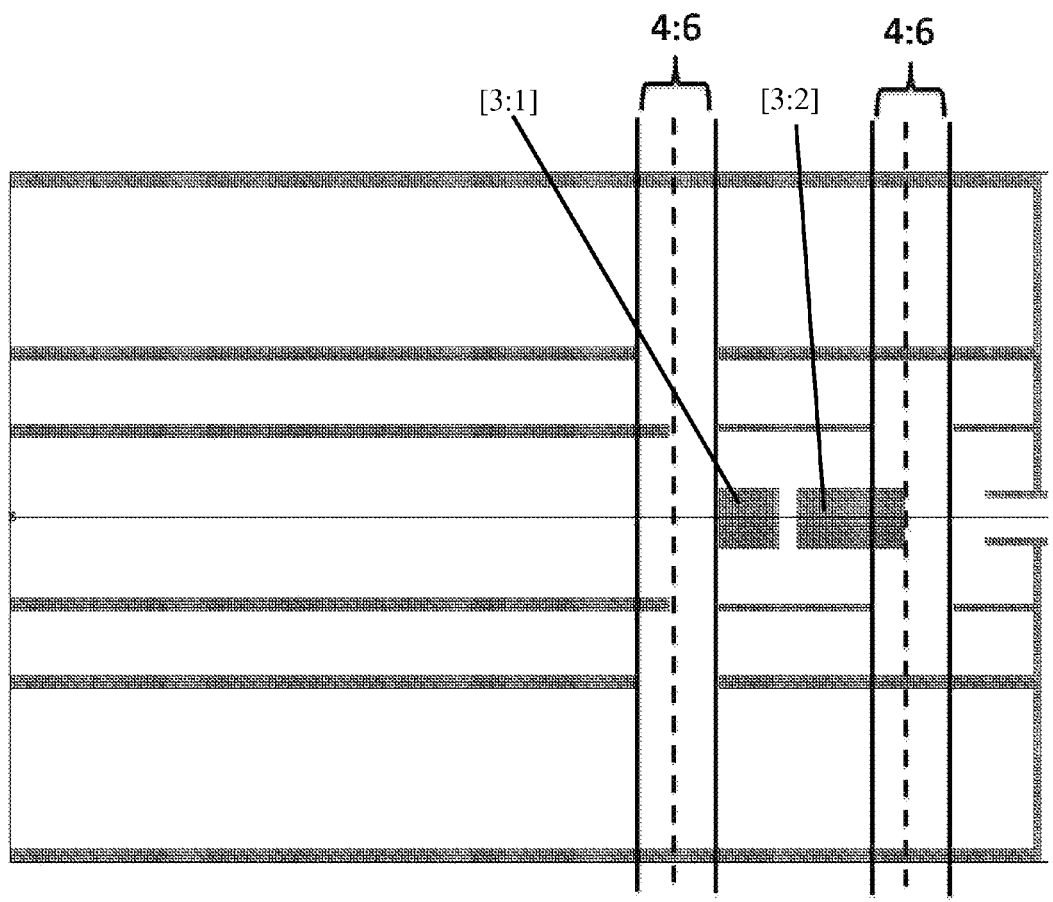
Figure 9:
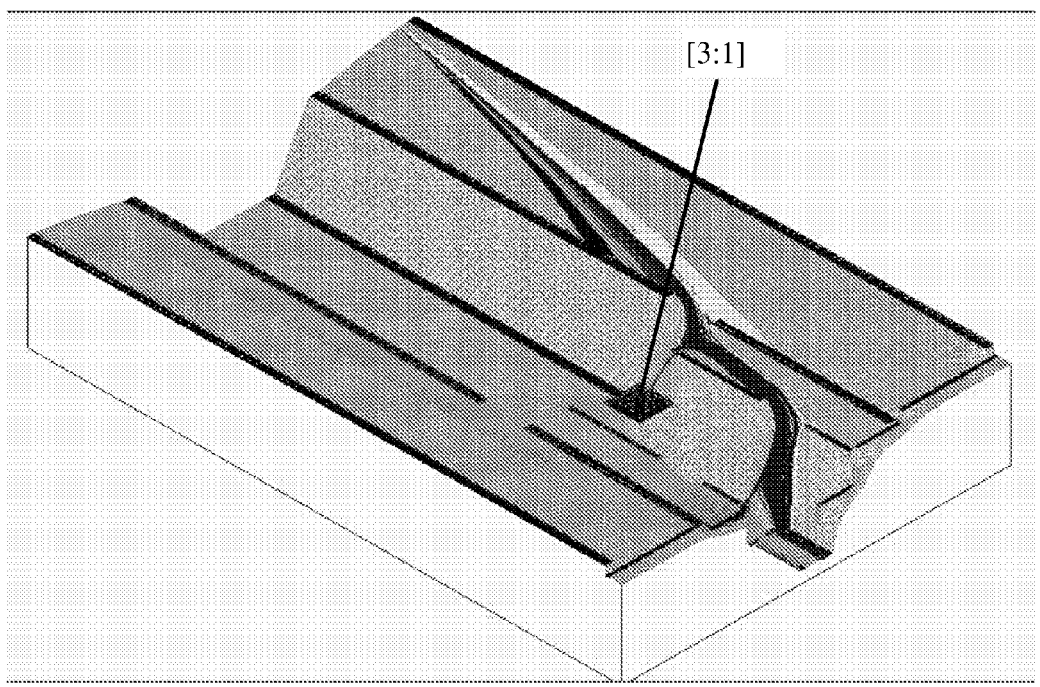
Figure 10:
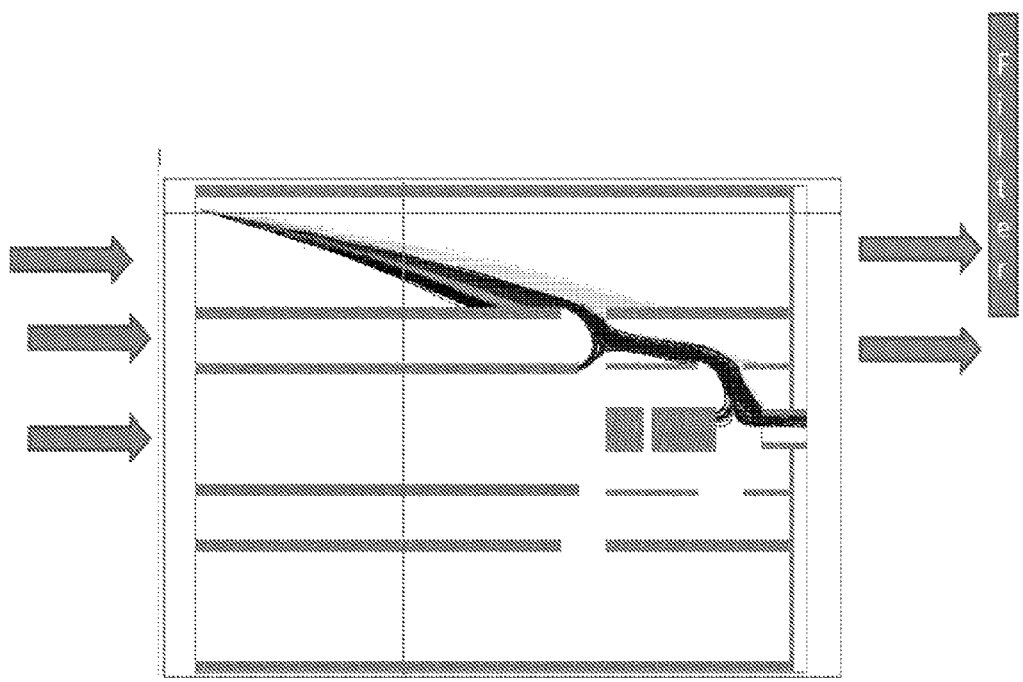
Figure 11:
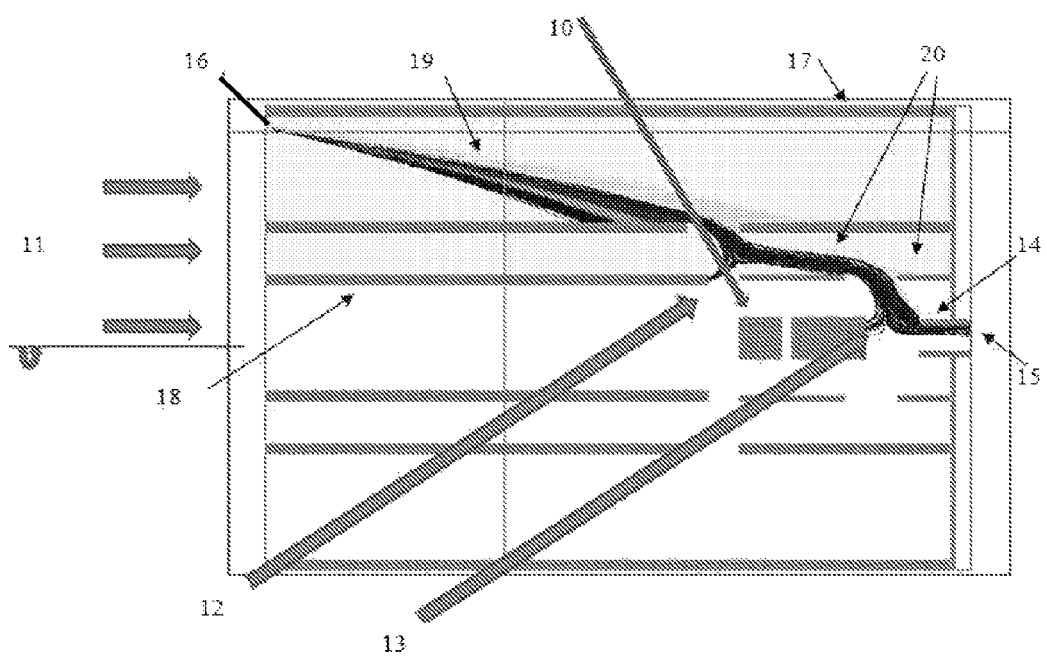

In another embodiment, the DMA apparatus are constructed as shown in FIG. 7. Here, electrodes (1,3) and (2,2) in FIG. 4 are replaced by plural electrodes shown in FIG. 7. The list of applied voltages is listed in Table 2.

TABLE 2

| Electrode | Applied Voltage in Volts (V) |
|---|---|
| [0,1] | 0 |
| [1,1] | −105 |
| [1,2] | −110 |
| [1,3] | −205 |
| [1,4] | −210 |
| [1,5] | −215 |
| [1,6] | −220 |
| [1,7] | −225 |
| [1,8] | −300 |
| [2,1] | −250 |
| [2,2] | −255 |
| [2,3] | −260 |
| [2,4] | −265 |
| [2,5] | −270 |
| [2,6] | −275 |
| [2,7] | −285 |
| [3,1] | −500 |
| [3,2] | −495 |
| [3,3] | −500 |

The primary purpose of having each such section or segment (and/or portion thereof) that can receive an electrical voltage different and/or independent from that of another section or segment (and/or portion thereof) is to assist a forward motion of particles in relatively slow sheath gas, typically in the same direction as the sheath gas flow. This produces extra electric mobility toward downstream and increases the transfer efficiencies in the very slow moving sheath flow often found in this $2^{nd}$ DMA stage. Similarly, an electrode used in the $1^{st}$ DMA stage may be replaced by multiple electrodes to produce the electric fields in the same direction as the sheath flow to promote Target Particle transfer efficiencies.

In another embodiment, the DMA apparatus has no inward cross flow through the gap, and particles are guided by filter electrodes which also eliminate unwanted particles which happen to pass through the gap by diffusion. By repetition of this process, this Q is kept minimal while achieving high transfer efficiency and resolving power. In one embodiment, the Target $Q_c$ is <0.7 ml/s. A cutaway of a cascade-type DMA is depicted in FIG. 2. Here, the smaller particles are eliminated by the guiding electrodes, which show a sharp cutoff in signals. Larger particles with inward diffusion will be eliminated by the electrodes shown in left (high mass filter, Arrow 30). The guiding electrode will not only function as the low mass filter, but also will "guide" the Target Particles at the middle portion of tube to minimize wall loss at the exit tube (Arrow 31). This is distinguishable from the related art because here, the non-target particles do not travel laterally from the outer cavity to the inner cavity. Here, the sheath flow is removed before the target particles are removed through the exit end. As compared to the related art, little migrating through the gaps (or slits) occurs. Due to the varying size of each annular and central space, the amount of air inserted through each space is adjusted so that the pressure exerted is substantially equal. In some related art, high volume of air flow was pushed or pulled through a DMA, such as with suction, along with the sample of target particles, from the outward cavity to the inward cavity, draining at the exit end. Only a small concentration of the target particles was retrieved. This the instant embodiment, a higher concentration of Target Particles are extracted.

In another embodiment, the DMA apparatus has outward cross flow, with the amount of air inserted through the annular and central spaces being substantially equal. Again, the non-target particles do not travel laterally from the outer cavity to the inner cavity, but rather from the inner cavity to the outer cavity. One significant advantage for these two embodiments is that the exit flow is small, so that the flow rate exiting (with the target particles) is small. In one embodiment, approximately 1 mL/s exits, rather than 3 L/min from the related art. This results in highly concentrated target particles, which can then be used in a mass spectrometer or other analyzer.

FIG. 3 shows the separation of the groups of ions having the same m/z (mass/charge) ratio. Since MS ("Mass Spectrometry") cannot separate these groups, pre-filtering via an ionization method such as electrospray (ESI) which produces highly charged molecules may become useful. Note here that the ion counts in the simulation are reduced due to the excessive Coulombic repulsion. It is due to the whole packet being released at the point source (the axisymmetric design of this apparatus in this particular modeling process), but it does not happen in reality.

FIG. 3 shows one embodiment of the DMA 100 showing the housing 102. Inlet 96 provides aerosol particles 98 into the housing pathway 104 of the housing 102. Two conduits 106, 114 are located radially inwards from the housing 102. First conduit 106 forms a first pathway 118. Second conduit 114 forms a second pathway 128. Exit conduit 134 forms the exit pathway 138. The aerosol particles 98 flow from inlet 96 longitudinally downstream to the exit pathway 138.

Outer walls 108, 112 separate the housing pathway 104 from the first conduit pathway 118. The outer walls 108, 112 are located radially inward from the housing 102. Outer wall 108 is located longitudinally upstream from the outer wall 112. A first outer aperture 110 is located between the outer walls 108, 112. The first outer aperture 110 provides access between the housing pathway 104 and the first pathway 118.

Inner walls 116, 122, 126 separate the first pathway 118 from the second pathway 128. The inner walls 116, 122, 126 are located radially inward from the housing 102 and the outer walls 108, 112. Inner wall 116 is located longitudinally upstream from the inner walls 122, 126. Inner wall 122 is located longitudinally upstream from inner wall 126. A first inner aperture 120 is located between the inner walls 116, 122. A second inner aperture 124 is located between the inner walls 122, 126. The inner apertures 120, 124 provide access between the first pathway 118 and the second pathway 124.

Exit wall 136 separates the second pathway 128 from the exit pathway 138. Block electrodes 130, 132 are located longitudinally upstream from the exit wall 136 and exit pathway 138.

Computational Methods. A Statistical Jump Diffusion(1) (SJD) program and direct numerical simulation package was used to transport the molecule by adding averaged random spread on the projectile's expected destination determined by the local electrostatic and aerodynamic field. This stochastic approach is preferred over the direct deterministic trajectory approach, due to the astronomical number of collisions. Trajectories of large molecules depend on density, size, shape and other factors, and are characterized by dimensionless Stoke, Knudsen and Peclet numbers. In this study, SJD has been modified to satisfy the known particle behavior (i.e. aerosol dynamics) and tested in some well known velocity field calculated. Slip correction, relaxation time, and shape factor parameter are introduced. The diffusional spread is assumed to follow the square root law. All electrostatic fields are calculated by existing Laplace solver in SIMION program. Finally, the gas flow inside the newly developed differential mobility regions has been modeled by a commercial fluid dynamics package to provide accurate particle trajectories.

Stoke friction, including Cunningham slip correction, is used as a correction to predict the better approximation to frictional force between fluid and a particle moving through this fluid. The slip correction factor can be defined as $$C = 1 + \frac{2l}{d_p}\left(1.257 + 0.4\exp\left(\frac{-0.55d_p}{l}\right)\right)$$

wherein the variables of the slip correction are:
C is the correction factor;
l is the mean free path; and
d is the particle diameter.

The embodiment of the invention depicted in FIG. 4 increases the number of electrode portions; for example, the lower segment of the medial electrode includes an inner wall segment having electrode portions (1,3) through (1,8), and the middle section of the central electrode includes electrode portions (2,2) through (2,6). The primary purpose of having each such section or segment (and/or portion thereof) that can receive an electrical voltage different and/or independent from that of another section or segment (and/or portion thereof) is to assist a forward motion of particles in relatively slow sheath gas, typically in the same direction as the sheath gas flow. The success of detection or separation of Target Particles typically is a function of the differential reaction of different types of particles to the downstream flow of sheath gas (and/or sample carrier gas), each particle's size and electrical charge, and the relative intensities and lengths and configurations of the electrical fields established within the airflow pathways. Such detection and/or separation of Target Particles may be maximized by optimizing the voltage parameters of the system of such electrode sections and segments (and/or portions thereof), in accordance with the gas flow rate(s) and the size and charge of the Target Particles.

In one specific embodiment of the invention:
(a) said upstream segment of said medial electrode (1,1) has a negative electrical voltage of about −105 volts; said downstream segment of said medial electrode has an outer portion (1,2) having a negative electrical voltage of about −105 volts; said downstream segment of said medial electrode has successive downstream inner portions having the following respective negative voltages: (1,3)=−205 volts; (1,4)=−210 volts; (1,5)=−215 volts; and (1,6)=−220 volts; (1,7)=−225 volts; and (1,8)=−300 volts;
(b) said upper section of said central electrode (2,1) has a negative electrical voltage of about −250 volts; said middle section of said central electrode has successive downstream portions having the following respective negative voltages: (2,2)=−255 volts; (2,3)=−260 volts; (2,4)=−265 volts; (2,5)=−270 volts; and (2,6)=−275 volts; said lower section of said central electrode (2,7) has a negative electrical voltage of about −285 volts; and
(c) said first block electrode (3,1) has a negative electrical voltage of about −500 volts; said second block electrode has a negative electrical voltage of about −495 volts; and said exit electrode-tip (3,3) has a negative electrical voltage of about −500 volts.

Those skilled in the art who have the benefit of this disclosure will appreciate that it may be used as the creative basis for designing devices or methods similar to those disclosed herein, or to design improvements to the invention disclosed herein; such new or improved creations should be recognized as dependent upon the invention disclosed herein, to the extent of such reliance upon this disclosure.

I claim:

1. A differential mobility analyzer apparatus for analyzing a sample of aerosol particles or for separating and concentrating aerosol particles, the apparatus comprising:
a housing serving as a conduit for the flow of aerosol particles, the housing defining a housing pathway for the flow of the particles along a longitudinal axis;
an inlet providing the particles into the housing, the particles flowing downstream along the longitudinal axis;
a first conduit located laterally inner of the housing, the first conduit defining a first pathway for the flow of the particles along the longitudinal axis;
a second conduit located laterally inner of the first conduit, the second conduit defining a second pathway for the flow of the particles along the longitudinal axis;
a first outer wall of the first conduit, the first outer wall separating the housing pathway from the first pathway wherein a voltage is applied to the first outer wall; and
a first inner wall of the second conduit, the first inner wall separating the first pathway from the second pathway wherein a voltage is applied to the first inner wall; and
a second outer wall of the first conduit located longitudinally downstream from the first outer wall, the second outer wall separating the housing pathway from the first pathway wherein a voltage is applied to the second outer wall.

2. A differential mobility analyzer apparatus for analyzing a sample of aerosol particles or for separating and concentrating aerosol particles, the apparatus comprising:
a housing serving as a conduit for the flow of aerosol particles, the housing defining a housing pathway for the flow of the particles along a longitudinal axis;
an inlet providing the particles into the housing, the particles flowing downstream along the longitudinal axis;
a first conduit located laterally inner of the housing, the first conduit defining a first pathway for the flow of the particles along the longitudinal axis;
a second conduit located laterally inner of the first conduit, the second conduit defining a second pathway for the flow of the particles along the longitudinal axis;
a first outer wall of the first conduit, the first outer wall separating the housing pathway from the first pathway wherein a voltage is applied to the first outer wall; and
a first inner wall of the second conduit, the first inner wall separating the first pathway from the second pathway wherein a voltage is applied to the first inner wall; and
a second inner wall of the second conduit located longitudinally downstream from the first inner wall, the second inner wall separating the first pathway from the second pathway wherein a voltage is applied to the second inner wall.

3. The apparatus of claim 2 wherein the first outer wall terminates longitudinally upstream of the first inner wall.

4. The apparatus of claim 2 further comprising:
a second opening in the second conduit that starts at the termination of the second inner wall, the second opening in the second conduit providing access for the flow of particles between the first pathway and the second pathway.

5. The apparatus of claim 4 further comprising:
an exit conduit located laterally inner of the second conduit, the exit conduit defining a exit pathway for the flow of the particles along the longitudinal axis, the exit conduit located laterally downstream from the second opening in the second conduit.

6. The apparatus of claim 5 further comprising:
an exit wall of the exit conduit located laterally downstream of the second opening in the second conduit wherein a voltage is applied to the exit wall, the exit wall separating the exit pathway from the second pathway.

7. The apparatus of claim 6 further comprising:
a third inner wall of the second conduit located longitudinally downstream from the second inner wall, the third inner wall separating the first pathway from the second pathway wherein a voltage is applied to the third inner wall, wherein the third inner wall starts longitudinally upstream of the exit wall.

8. The apparatus of claim 7 further comprising:
a first block electrode located laterally inward of the second conduit wherein the first block electrode starts at a position along the longitudinal axis equivalent to the second inner wall.

9. The apparatus of claim 8 further comprising:
a second block electrode located laterally inward of the second conduit wherein the second block electrode extends longitudinally downstream of the second inner wall.

10. The apparatus of claim 9 wherein the radially outermost surface of the first block electrode, the second block electrode, and the exit conduit are equivalent.

11. The apparatus of claim 10 wherein the inlet introduces the aerosol particles into the housing pathway.

12. The apparatus of claim 6 further comprising:
a third inner wall of the second conduit located longitudinally downstream from the second inner wall, the third inner wall separating the first pathway from the second pathway wherein a voltage is applied to the third inner wall, wherein the third inner wall starts longitudinally upstream of the exit wall.

13. A differential mobility analyzer apparatus for analyzing a sample of aerosol particles or for separating and concentrating aerosol particles, the apparatus comprising:

a housing serving as a conduit for the flow of the aerosol particles, the housing defining a housing pathway for the flow of the particles along a longitudinal axis, the housing having a cross section sized at a housing diameter;

an inlet providing the particles into the housing, the particles flowing downstream along the longitudinal axis;

a first conduit located radially inner of the housing, the first conduit defining a first pathway for the flow of the particles along the longitudinal axis, the first conduit having a cross section sized at a first diameter;

a second conduit located radially inner of the first conduit, the second conduit defining a second pathway for the flow of the particles along the longitudinal axis, the second conduit having a cross section sized at a second diameter;

a first outer wall separating the housing pathway from the first pathway wherein a voltage is applied to the first outer wall, the first outer wall forming a conduit having a cross section with a diameter of the first diameter; and a first inner wall separating the first pathway from the second pathway wherein a voltage is applied to the first inner wall, the first inner wall forming a conduit having a cross section with a diameter of the second diameter;

wherein the first outer wall terminates longitudinally upstream of the first inner wall;

a second outer wall forming a conduit having a cross section with a diameter of the first diameter, the second outer wall located longitudinally downstream from the first outer wall, the second outer wall separating the housing pathway from the first pathway wherein a voltage is applied to the second outer wall;

a second inner wall forming a conduit having a cross section with a diameter of the second diameter, the second inner wall located longitudinally downstream from the first inner wall, the second inner wall separating the first pathway from the second pathway wherein a voltage is applied to the second inner wall;

wherein the most upstream portion of the second outer wall starts at a position along the longitudinal axis equivalent to the most upstream position of the second inner wall.

14. The apparatus of claim 13 further comprising:

a first outer opening longitudinally between the first outer wall and the second outer wall wherein the first outer opening starts at the termination of the first outer wall, the first outer opening providing access for the flow of particles between the housing pathway and the first pathway;

a first inner opening longitudinally between the first inner wall and the second inner wall wherein the first inner opening starts at the termination of the first inner wall, the first inner opening providing access for the flow of particles between the first pathway and the second pathway.

15. The apparatus of claim 14 further comprising:

a third inner wall forming a conduit having a cross section with a diameter of the second diameter, the third inner wall located longitudinally downstream from the first inner wall and the second inner wall, the third inner wall separating the first pathway from the second pathway wherein a voltage is applied to the third inner wall;

a second inner opening longitudinally between the second inner wall and the third inner wall wherein the second inner opening starts at the termination of the second inner wall, the second inner opening providing access for the flow of particles between the first pathway and the second pathway.

16. The apparatus of claim 15 further comprising:

an exit conduit located radially inner of the second conduit, the exit conduit defining an exit pathway for the flow of the particles along the longitudinal axis, the exit conduit located laterally downstream from the second inner opening, the exit conduit having a cross section sized at an exit diameter;

an exit wall forming a conduit having a cross section sized at the exit diameter, the exit wall located laterally downstream of the second opening in the second conduit wherein a voltage is applied to the exit wall, the exit wall separating the exit pathway from the second pathway.

17. A differential mobility analyzer apparatus for analyzing a sample of aerosol particles or for separating and concentrating aerosol particles, the apparatus comprising:

a housing serving as a conduit for the flow of the aerosol particles, the housing defining a housing pathway for the flow of the particles along a longitudinal axis, the housing having a cross section sized at a housing diameter;

an inlet providing the particles into the housing at the housing pathway, the particles flowing downstream along the longitudinal axis;

a first conduit located radially inner of the housing, the first conduit defining a first pathway for the flow of the particles along the longitudinal axis, the first conduit having a cross section sized at a first diameter;

a second conduit located radially inner of the first conduit, the second conduit defining a second pathway for the flow of the particles along the longitudinal axis, the second conduit having a cross section sized at a second diameter;

a first outer wall separating the housing pathway from the first pathway wherein a voltage is applied to the first outer wall, the first outer wall forming a conduit having a cross section with a diameter of the first diameter; and a first inner wall separating the first pathway from the second pathway wherein a voltage is applied to the first inner wall, the first inner wall forming a conduit having a cross section with a diameter of the second diameter;

wherein the first outer wall terminates longitudinally upstream of the first inner wall;

a second outer wall forming a conduit having a cross section with a diameter of the first diameter, the second outer wall located longitudinally downstream from the first outer wall, the second outer wall separating the housing pathway from the first pathway wherein a voltage is applied to the second outer wall;

a second inner wall forming a conduit having a cross section with a diameter of the second diameter, the second inner wall located longitudinally downstream from the first inner wall, the second inner wall separating the first pathway from the second pathway wherein a voltage is applied to the second inner wall;

wherein the most upstream portion of the second outer wall starts at a position along the longitudinal axis equivalent to the most upstream position of the second inner wall;

a first outer opening longitudinally between the first outer wall and the second outer wall wherein the first outer opening starts at the termination of the first outer wall, the first outer opening providing access for the flow of particles between the housing pathway and the first pathway;

a first inner opening longitudinally between the first inner wall and the second inner wall wherein the first inner opening starts at the termination of the first inner wall, the first inner opening providing access for the flow of particles between the first pathway and the second pathway;

a third inner wall forming a conduit having a cross section with a diameter of the second diameter, the third inner wall located longitudinally downstream from the first inner wall and the second inner wall, the third inner wall separating the first pathway from the second pathway wherein a voltage is applied to the third inner wall;

a second inner opening longitudinally between the second inner wall and the third inner wall wherein the second inner opening starts at the termination of the second inner wall, the second inner opening providing access for the flow of particles between the first pathway and the second pathway;

an exit conduit located radially inner of the second conduit, the exit conduit defining an exit pathway for the flow of the particles along the longitudinal axis, the exit conduit located laterally downstream from the second inner opening, the exit conduit having a cross section sized at an exit diameter;

an exit wall forming a conduit having a cross section sized at the exit diameter, the exit wall located laterally downstream of the second opening in the second conduit wherein a voltage is applied to the exit wall, the exit wall separating the exit pathway from the second pathway; and a third inner wall of the second conduit located longitudinally downstream from the second inner wall, the third inner wall separating the first pathway from the second pathway wherein a voltage is applied to the third inner wall, wherein the third inner wall starts longitudinally upstream of the exit wall.

* * * * *